United States Patent
Yan

Patent Number: 5,620,589
Date of Patent: Apr. 15, 1997

[54] CHEMICALLY ACTIVE VAPOR/LIQUID SEPARATOR

[75] Inventor: Tsoung Y. Yan, Wayne, Pa.

[73] Assignee: Mobil Oil Corporation, Fairfax, Va.

[21] Appl. No.: 367,413

[22] Filed: Dec. 30, 1994

[51] Int. Cl.⁶ ............ C10G 67/00; C10G 49/22; B01D 53/02; C07C 7/12
[52] U.S. Cl. ............ 208/97; 208/99; 208/100; 208/132; 208/262.1; 585/820; 95/131
[58] Field of Search ............ 208/97, 99, 100, 208/132, 262.1; 585/820; 95/131

[56] References Cited

U.S. PATENT DOCUMENTS

| | | | |
|---|---|---|---|
| 1,833,396 | 11/1931 | Gary | 208/286 |
| 2,034,712 | 3/1936 | Dolbear | 208/283 |
| 2,481,300 | 9/1949 | Engel | 196/36 |
| 3,403,198 | 9/1968 | Van Pool | 208/262.1 |
| 3,445,380 | 5/1969 | Urban | 208/286 |
| 3,445,381 | 5/1969 | De Graff et al. | 208/313 |
| 3,457,165 | 7/1969 | Urban | 208/283 |
| 3,516,924 | 6/1970 | Forbes | 208/65 |
| 3,861,900 | 1/1975 | Reusser | 208/299 |
| 4,123,351 | 10/1978 | Chapman et al. | 208/262.1 |
| 4,157,376 | 6/1979 | Vulikh et al. | 423/240 |
| 4,594,231 | 6/1986 | Nishino et al. | 423/210 |

OTHER PUBLICATIONS

Oil & Gas Journal Article—May 12, 1986.

*Primary Examiner*—Glenn A. Caldarola
*Assistant Examiner*—Patricia L. Hailey
*Attorney, Agent, or Firm*—Malcolm D. Keen; Thomas W. Steinberg

[57] ABSTRACT

Acidic halides, especially chlorides, in two phase (vapor and hydrocarbon liquid) reactor effluent are separated and at least the halides in the vapor fraction neutralized in a vapor/liquid separator with an alkaline neutralization medium such as an alumina treater impregnated with NaOH. The treater may remove halides from both the vapor and liquid phase within the separator.

17 Claims, 1 Drawing Sheet

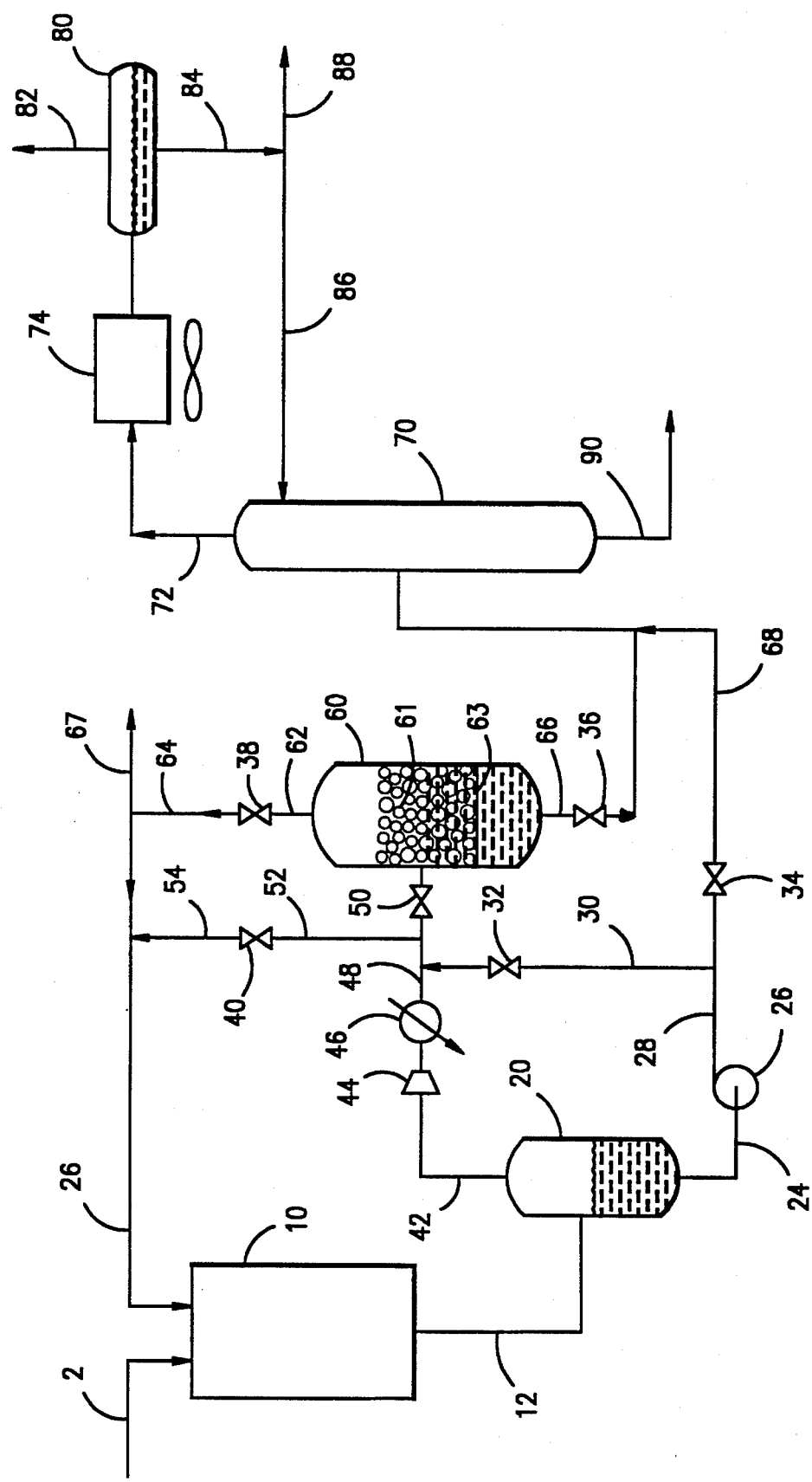

CHEMICALLY ACTIVE VAPOR/LIQUID SEPARATOR

CROSS-REFERENCE TO RELATED APPLICATIONS

This application is related to my prior co-pending application Ser. No. 08/217821 filed on Mar. 25, 1994.

This application is also related to other applications of mine filed simultaneously with this application directed to:

| DOCKET | TITLE |
| --- | --- |
| 08/367,500 | TWO PHASE TREATMENT OF VAPOR TO REMOVE HALIDES |
| 08/367,498 | REMOVAL OF ACIDIC HALIDES FROM GAS STREAMS |
| 08/367,501 | TWO PHASE REMOVAL OF HALOGENS FROM LIQUID HYDROCARBONS |
| 08/367,411 | THREE PHASE REMOVAL OF HALOGENS FROM LIQUID HYDROCARBONS |
| 08/367,499 | REMOVAL OF ACIDIC HALOGENS FROM HOT GAS STREAMS AND ATTRITION REGENERATION OF CAUSTIC |
| 08/367,412 | WASHING SALT FROM SOLID CAUSTIC WITH OIL |

FIELD OF THE INVENTION

This invention relates to neutralizing acidic halides, especially chlorides, in a hydrocarbon vapor/liquid separator.

BACKGROUND OF THE INVENTION

Many refinery and petrochemical processes involve separation of vapor from liquid phases, and subsequent neutralization or removal of acidic halogen species in either the vapor phase or the liquid phase in downstream processing steps. Several refinery processes (reforming and isomerization) are reviewed below, including a discussion as to why acidic halides are present in such streams, the difficulties caused by materials such as chlorides, and the problems of removing such acidic materials.

Catalytic reforming, using Pt based reforming catalyst, is one of the most important refinery processes in the world. Most refineries have a catalytic reformer, which converts naphtha fractions into high octane reformate.

Reformers come in many types and sizes—from 2000 BPD fixed bed units to moving or swing bed units processing more than 50,000 BPD. Reformers are available with fixed bed reactors, swing bed reactors, or moving bed reactors. Many new units are moving bed reactors, available from UOP, Inc, Des Plaines, Ill.

Reformers generally use mono-metallic catalysts (Pt on a support such as alumina) or bi-metallic catalyst (Pt-Re on a support). Other combinations of Pt and other metals are known.

All reforming catalysts are believed to contain halogen, almost invariably chlorine. Chlorine is now ubiquitous in catalytic reforming. Chloroplatinic acid may be used in the impregnation solution forming the catalyst. Some refiners may add chlorine compounds during normal operation.

One major oil company developed a Pt reforming catalyst regeneration or "rejuvenation" procedure which conducted at least some portions of the regeneration in the presence of one or more chlorine compounds. The procedure was believed originally developed for swing reactor systems which were regenerated every day or so, but this regeneration method, or some variant of it, was eventually used in semi-regenerative reformers and in moving bed reformers.

All of this chlorine can, and does, find its way into gas and liquid products from the reformer. Based on a review of several decades of The Oil and Gas Journal, the key to successful catalytic reforming is lots of chloride. For decades refiners have talked about the problems of getting enough chlorides into the system, and dealing with the chlorides in the vapor and liquid products from the reformer.

It should be clarified at this point that while most reformers use chlorines as a catalyst component, some may use other halogens, such as F or I, but Cl is the halogen of choice, so hereafter chlorine and its reaction or degradation products will be referred to rather than halogens in general.

In 1977 there was talk of the need for heat, chloride and moisture to redistribute platinum.

In 1980 there was a discussion of deposits of ammonium chloride in catalytic reforming compressor internals.

In 1985 there was discussion of the need for, and difficulty of maintaining, 1.0 wt % chloride on bimetallic catalyst between regenerations. It was suggested to "come out on the high side on chloride."

In Alumina adsorbents effectively remove HCl from reformer $H_2$ gas stream, Janke et al, Oil and Gas Journal, May 12, 1986, page 64, talked about controlled injection of organic chloride at the reformer reactor inlet, and the mischief caused by all this chloride. The problem was worse with continuous catalytic reforming processes, which were reported "to require higher levels of chloride addition for regeneration . . ." The solution proposed was use of alumina adsorbents to remove the $HC_1$ from the net off gas. This article is incorporated by reference.

In Apr. 1, 1994 there was a discussion of the problem of corrosion in fired heaters due to chloride in the hydrogen from the reforming unit. The proposed solution was to install alumina treaters.

All of our refineries have some problems with chlorides in reformate. Several of them have installed alumina treaters to remove chlorides from the entire recycle gas stream.

The problem is not limited to reformers. Similar problems occur in some isomerization units, and may occur in other units which are dry and use a chloride containing catalyst.

The conditions which lead to chloride problems are catalysts which contain, or reaction conditions which require, chlorine compounds, and reactants which are dry enough that no separate aqueous phase forms in the vapor/liquid separator downstream of the reactor. Essentially all Pt reformers meet these conditions, and many isomerization and other processing units meet these conditions.

The situation could be summarized as follows for Pt reformers. Although refiners may use different reforming catalysts, all the catalysts seem to contain chlorine. There is enough chlorine either present in the virgin catalyst, or from chlorine addition during reformer operation, or from chlorine added during the catalyst regeneration, so that chlorine compounds appear in all the product streams coming from the reformer. Both vapor and liquid products have chlorine compounds, usually referred to as chlorides in most refineries, and these cause many problems.

The raw liquid reformate has chlorides. The net hydrogen gas make has chlorides. When raw reformate is fractionated, usually in a debutanizer, the overhead fractions contain chlorine compounds, unless the chlorides form salts which come out in the debutanizer and plug it.

To solve the problem of removing chlorides from gas streams, refiners have generally used beds of solid adsorbents, such as alumina impregnated with an alkaline material such as NaOH. Such approaches are discussed in the 1994 and 1986 OGJ articles discussed above, and are used commercially. While these approaches work, there are problems associated with the use of such alumina beds. The problems can include one or more of: cost, catalytic activity, regeneration and disposal.

Alumina beds are relatively costly, in terms of the amount of active ingredient present. The alumina typically contains 5 to 10 wt % caustic. Alumina costs more than caustic, and the alumina primarily serves as a support, but one which unfortunately is not always inert.

Alumina beds can exhibit catalytic activity. When alumina beds are used to remove chlorides from flowing vapor streams, aluminum chloride can form, and cause catalytic reactions which convert some of the hydrocarbon vapor species into a much higher molecular weight material. In some units, the gas is turned to goo, at least enough is formed that the effectiveness of the alumina bed is much impaired. This heavy viscous material must be removed to "regenerate" the alumina bed, so that it may be used to absorb additional amounts of chlorides or other acidic components from the flowing gas stream. Steam stripping will usually "regenerate" such a bed.

Disposal of solid adsorbents can be a serious waste management problem. Solid bed adsorbents must eventually be retired and frequently contains too much hydrocarbon to permit dumping in a landfill. The adsorbent bed may be steam stripped as a prelude to disposal. The resulting water/ hydrocarbon product must be stripped to remove benzene from the waste water. The benzene and lighter hydrocarbons removed from the waste water are usually incinerated, and some of the chlorides may eventually end up as HCl, produced during the incineration of the benzene rich hydrocarbon phase.

I studied the problem of chloride removal from reformer vapor streams and realized that many of the problems could be overcome by a different approach.

Based on experimental work, I found that chlorides could be efficiently removed from a vapor stream in the presence of large amounts of liquid hydrocarbon. It was also possible to remove chlorides from hydrocarbon liquid, in the presence of large amounts of vapor.

By neutralizing or chemical reacting acidic halides at the same time as, and in the same vessel performing, vapor/ liquid separation, it was possible to efficiently treat one, or the other, or preferably both streams at the same time. Not only was the chloride removal unexpectedly efficient, it also avoided most or all of the capital expense of a separate treater vessel.

Thus to remove chlorides from reformer recycle gas and reduce the amount of chlorides in reformate, I let a vapor/ liquid separator associated with the reformer perform both the job of chloride removal and of vapor/liquid separation.

This approach not only saves money, it overcomes one difficulty associated with alumina treaters and gas streams. The difficulty is the polymer or goo that forms when chlorides in the gas exhaust enough caustic to form some AlCl3 catalyst from the alumina support used. Until now, there was no good way to remove this material, and some refiners had to provide swing bed treaters and go through troublesome stripping procedures to get the polymer off.

In my process, the polymer formed in the alumina treaters may be continuously washed off the alumina treater by the large amounts of reformate present in such separators. The minuscule amounts of high molecular weight material formed by the alumina treater will not be troublesome in the reformate, indeed they will generally be washed off as soon as polymerization (or oligomerization) proceeds far enough to produce liquids. Thus the life of the alumina treater can be extended significantly.

In fact, according to stoichiometric calculations, the loading capacity of a typical alumina adsorber should be 10–12 g of chloride/100 g of alumina. In actual practice, the loading capacity is found to be around 5 or 6 g Cl/100 g alumina. The loading capacity of alumina treaters in actual commercial use in this service is believed reduced at least in part to the build up of polymeric materials which cover the adsorption sites.

While the alumina treaters will eventually become spent, they will usually not need hot inert stripping to remove viscous oils formed on them, and will therefore have a higher on stream time. Many refiners will also have the ability, or for minor capital cost may acquire the ability, to change out the alumina treaters without shutting down the unit.

In many reformers, there are two vapor/liquid separators, though usually only the first one is called a separator. The reactor effluent is cooled and separated in a first vapor liquid separator. The gas is compressed, cooled, and recontacted with reformate or liquid from the first vapor liquid separator in a recontacting drum. This recontacting drum is a second vapor liquid separator. Alumina treaters may be put in either separator, or both, and this double treatment may provide enough reserve treating capacity that the unit will not need to shut down for alumina treater replacement until the next scheduled refinery turnaround.

A refiner may also provide piping and valves so that, for a day or a few days, one or the other of the separators may be isolated from service so that the alumina treaters in a given separator may be replaced. Thus the two V/L separators, which are already present in most recently built reformers, can serve as "swing reactors", or at least can provide a way to isolate one of the separators for servicing. Temporarily removing, e.g., the recontacting drum from service would not shut down the reformer. It would merely increase the molecular weight of the recycle gas, putting more load on the recycle gas compressor. All that happens to the unit is that the recycle gas flow drops some, or catalyst aging rates increase some, and hydrogen purity of the recycle and off gas drops a little. Many reformers have run without ever having a recontacting drum, so the loss of one separator for a few days can be easily tolerated.

The commercially proven alumina treaters will be preferred by many refiners for use in the vapor/liquid separator. These devices are mechanically strong, and will not plug or add anything detrimental to the recycle gas. I have also developed other methods of neutralizing acidic halides when both large amounts of hydrocarbon liquid and vapor are present which are potentially longer lasting and less costly. These are suitable for use herein.

BRIEF SUMMARY OF THE INVENTION

Accordingly, the present invention provides a process for a process for removing acidic halides in a vapor and hydrocarbon liquid two-phase mixture and separating said mixture into a vapor phase and a liquid phase comprising: charging to a vapor/liquid separator operating at vapor/liquid separation conditions a two phase mixture of liquid hydrocarbons and vapor, and wherein said liquid, said vapor or both contain acidic halogen components; separating said two phase mixture into a vapor rich phase and a liquid phase in said separator and removing within said separator at least a majority of said acidic halogen components by reaction with an alkaline reagent within said separator; and separately removing a vapor phase and a liquid phase from said separator as a product of the process.

In another embodiment, the present invention provides a reforming process comprising charging to a reforming reactor containing a chlorine and platinum containing reforming catalyst operating at reforming conditions a naphtha boiling range feed and a recycle hydrogen gas stream to produce a reforming reactor effluent comprising hydrogen rich vapor and naphtha boiling range reformate and chlorides; cooling said reactor effluent to produce a two phase mixture; neutralizing and separating said two phase mixture in a neutralizing separator comprising: an inlet for a two phase, vapor liquid mixture, an outlet in an upper portion thereof for a vapor phase, an outlet in a lower portion thereof for a liquid phase, and a bed of alkaline neutralizing material disposed within said separator at an elevation intermediate said upper portion and said lower portion, and in a location within said separator wherein said neutralizing material is continuously or intermittently contacted by reformate liquid; removing from said separator a neutralized vapor stream and recycling at least a portion thereof to said reforming reactor, and removing from said separator a liquid reformate fraction as a product of the process.

In yet another embodiment, the present invention provides a process wherein said reformer comprises a low pressure vapor/liquid separator and a higher pressure recontacting drum, cooled reactor effluent is first charged to said low pressure separator, vapor from said low pressure separator is compressed to a higher pressure, liquid from said pressure separator is pumped and recontacted with compressed vapor from said low pressure separator to form a higher pressure mixture; said high pressure mixture is separated in said recontacting drum to produce a high pressure vapor phase at least a portion of which is recycled to said reforming reactor and a high pressure liquid phase which is removed as a product of the process, and wherein said alkaline reagent is present in at least one of said low pressure separator and said recontacting drum.

BRIEF DESCRIPTION OF THE DRAWINGS

The FIGURE is a simplified schematic view of a preferred neutralizing separator in a catalytic reforming unit.

DETAILED DESCRIPTION OF PREFERRED EMBODIMENTS

The invention can be better understood in conjunction with a review of the Figure which shows a neutralizing vapor/liquid separator in a reformer. Much of the flow of vapor and liquid could be considered a highly simplified version of the flow shown in U.S. Pat. No. 3,516,924, which is incorporated by reference and which shows the use of a recontacting drum.

The Pt reformer is shown largely as a box 10, to which feed in 2 and recycle hydrogen in line 26 are added and from which reactor effluent is removed via line 12. Not shown are heaters, pumps, valves and much other process equipment. Many types of reforming reactors may be used, such as the Moving Bed Contacting Process disclosed in U.S. Pat. No. 4,102,776, Stone. Another reforming reactor design which may be used is the hybrid design using a gravity-flowing system, as disclosed in U.S. Pat. No. 3,864,240, Stone. Reforming reactors are readily available.

Chlorine or compounds thereof will usually be injected either with the feed, or added directly or indirectly via catalyst regeneration. The reactor effluent vapor, after heat exchange with feed and cooling by means not shown, is charged via line 12 to vapor liquid separator 20. A recycle hydrogen stream is withdrawn from the separator via line 42 and a reformate liquid stream is withdrawn via line 24. The gas phase is compressed in compressor 44 and cooled in cooler 46 and mixed in line 48 with the liquid phase from the separator, which is passes through pump 26 and lines 28 and 30 to line 48 to mix with the compressed vapor. The mixture is then discharged into recontacting drum 60, which could also correctly be called a second vapor/liquid separator.

In separator 60 alumina treaters, shown as relatively large balls of alumina, are disposed as a bed 61 supported by screen or grid means 63. Chlorides in the reactor effluent, whether in the vapor or the liquid, will be effectively removed by contact with an alkaline treating medium in the vapor liquid separator 60. A treated gas phase is withdrawn via lines 62 and 64 and recycled via line 26 to reactor 10. The net gas make is withdrawn via line 67.

Reformate liquid is withdrawn from the separator via line 66 and charged to fractionator 70, typically a debutanizer. A debutanized reformate is removed from the base of the fractionator via line 70, while an overhead vapor fraction is removed via line 72, cooled in fin fan cooler 74 and then separated in overhead receiver 80. A vapor phase is withdrawn via line 82 while a liquid phase is removed via line 84, with a portion returned as reflux to the column via line 86 and a portion withdrawn as a light liquid product via line 88.

Because the entire reformate effluent was treated in recontacting drum 60, it will usually not be necessary to remove chlorides from any of the streams downstream of drum 60. It will not be necessary to remove chlorides from reformate in line 66 as they have already been removed. The debutanizer overhead receiver vapor stream in line 82 will usually not require further treating, and may be burned as fuel or used in other refinery processes without fear of corrosion. The debutanizer 70 may be operated for extended periods without plugging (from salt deposits) or corrosion.

The alumina bed, or other alkaline treating material, may be periodically removed from service or bypassed, for replacement or bed rejuvenation. The recontacting drum would first be isolated by closing valves 50, 36 and 38. This would allow purging of the recontacting drum and entrance for maintenance.

Fairly normal operation of the reformer could continue by opening valve 34 and closing valve 32, so that the liquid phase from vapor liquid separator 20 could be charged directly to the debutanizer via line 68. Recycle gas flow would be maintained by opening valve 40 so that compressed recycle gas could flow directly to the reforming reactor via line 54 and 26, rather than to the recontacting drum 60.

More details will now be provided about each part of the process.

CATALYTIC REFORMING

This process is well known and widely used, most refineries have catalytic reforming units. Essentially all catalytic reformers operate with chlorine addition, either to the catalyst prior to startup, to the feed during normal operation, or as part of a continuous catalyst regeneration unit associated with a moving bed reformer.

Reformers are available from several licensors. UOP Inc, Des Plaines, Ill. will provide both fixed and moving bed reforming units.

Conventional reforming conditions can be used, including a temperature of 850° to 1050° F., a pressure of atmospheric to 500 psig and a LHSV of 0.1 to 10 Hr-1. Most reformers operate with recycle hydrogen, with from a 1:1 to 10:1 $H_2$:hydrocarbon mole ratio.

CHLORINE IN REFORMATE

Moving bed units frequently produce reformate with more than 0.5 wt ppm Cl, and often in excess of 1 wt ppm $C_1$, and sometimes with 2 or 3+ wt ppm Cl. Fixed bed units operating with large amounts of Cl addition due to catalyst demands or imminent shutdown for regeneration can produce reformate with like amounts of Cl, though typically moving bed units have the highest Cl levels.

Chlorine levels may be continuously, or intermittently, troublesome. Chlorine in reformate will usually be highest just before regeneration (for fixed bed units) or just before replacement of catalyst (in the case of moving bed units).

Some refiners may use other halogens such as F in full or partial replacement of Cl. My process will efficiently capture these materials as well.

Many refinery streams besides platinum reformers have this problem, as can be seen from the following discussion.

GAS STREAM WITH ACIDIC COMPONENTS

The process can be used with any gas stream containing acidic halogen compounds which can react with alkaline materials, including promoted alumina and solid caustic.

The gas stream can be mostly hydrocarbon vapors and hydrogen, or inert, or an oxidizing atmosphere such as air or flue gas with minor amounts of air.

Details on some of the types of acidic halides present in refinery streams, and the salts they form, are disclosed in *Calculations estimate process stream depositions,* Oil & Gas Journal, Jan. 3, 1994 pp 38–41, Yiing-Mei Wu. This article is incorporated by reference. It is cited to provide details on some of the many chemical species which exist in refinery and petrochemical streams.

Among the most ubiquitous halides are the chlorides, which are discussed extensively in the OGJ article above, and which cause so much mischief in refineries, and especially around and downstream of reformers. The reformer recycle gas, reformer off gas, and gas streams associated with reformer fractionators such as the off gas from the reformer debutanizer overhead receiver frequently have chloride levels higher than desired.

The gas stream can be dry or wet, i.e., contain some entrained water or have a significant water vapor pressure. In a reformer the gas streams will almost invariably be dry, most have less than 10 ppmv water, though some might have levels higher than this, on the order of 50 ppmv or perhaps even as high as 100 ppmv.

The gas streams charged to a vapor liquid separator of the invention will have large amounts of liquid hydrocarbons present. The process tolerates large amounts of liquid hydrocarbons, and even overcomes many of the problems encountered with alumina treaters, namely the buildup of viscous polymer or goo. The constant washing of, e.g., alumina treaters, with reformate removes polymers as quickly as they may form. The caustic impregnated on the alumina will eventually become exhausted, but the treaters will not lose effectiveness because of the buildup of polymer.

While alumina treaters will be preferred by many refiners, because they are such a known and safe material, other types of alkaline reagents may be used to remove acidic halides from a reactor effluent stream in a vapor liquid separator.

Suitable alkaline reagents include other completely "dry" or non-aqueous systems, as well as systems based on use of an aqueous alkaline material. The "dry" systems will be reviewed first, followed by a review of the aqueous systems.

DRY ALKALINE TREATING PROCESSES

As stated above, many refiners will prefer to use conventional alumina treaters impregnated with caustic solution. These are available commercially from many vendors.

Caustic impregnated charcoal or carbon or activated carbon may be used. Preparation of caustic impregnated carbons is an ancient art, used for gas masks and gas purification for over half a century. U.S. Pat. No. 1,781,664 disclosed use or pumice or coke impregnated with alkalies for gas purification.

Solid caustic may also be used. Either beads, pellets, pills, flakes, or solid caustics mixed with various supports or fillers. While use of pure NaOH—technical grade rather than reagent grade—is preferred for low cost, other materials such as glassmakers alkali (a mixture of about 20% $Ca(OH)_2$+80% NaOH), or KOH, soda lime, and like materials may also be used, though not necessarily with equivalent results.

Preferably the solid caustic is non-porous, and has a large void volume. Non-porous caustics are much less likely to crumble or collapse than porous materials. A large void volume will reduce the pressure drop associated with fluid flow through the bed, and provides space for salt crystals to form and accumulate.

TREATER BED DESIGN

The alkaline material may be disposed as a single fixed bed, moving bed, multiple fixed beds, or fluidized bed. For simplicity, most refiners will prefer to use a simple fixed bed, with either large particles of a mechanically strong alkaline solid, or to use prefabricated alumina treating material.

AQUEOUS PHASE TREATING SYSTEMS

It is also possible to remove acidic halides in the vapor/liquid separator using some means for providing constrained access of an aqueous alkaline treating material and the vapor and liquid phases charged to the extractor.

A caustic soaked charcoal bed may be used, as disclosed in my prior co-pending application Ser. No. 08/217821 filed on Mar. 25, 1994, which is incorporated by reference.

A new type of extraction process, using an aqueous phase under a hydrocarbon continuous phase, has recently been developed by me and may also be used.

As practiced in a reformer V/L separator, this process involves four phases (hydrogen rich gas, liquid reformate, and solid caustic under an aqueous film), and could be called a quadriphase extraction process.

REACTIVE QUADRIPHASE EXTRACTION

This process is very simple. Gas passes over solid caustic which will be immersed in, or splashed by, liquid hydrocarbon in the vapor liquid separator. No water need be added, nor any other chemicals except for the initial load of solid caustic.

The transport phenomena involved are complex—involving transport from a solid phase (solid caustic) through two immiscible phases (an aqueous film on the solid caustic, and a hydrocarbon coating on the aqueous film) to a gas phase.

Although it is not known for certain what transport phenomenon are at play here, it is believed that acidic halogen components pass through the gas and hydrocarbon phases to reach the aqueous phase. Solid caustic dissolves to reach the aqueous phase, where the neutralization reaction is believed to occur. Simple neutralization reactions are involved which proceed rapidly and completely which makes the process effective.

The reaction products remain in the water of reaction which forms a skin or film upon the solid caustic particles. The water dissolves the NaCl formed to produce brine which settles at the bottom of the separator. The solid caustic may be in the form of pure particles of a suitable caustic material, such as NaOH, KOH, CaO, MgO and the like. NaOH and KOH are preferred, and use of NaOH is most preferred.

This material may be extruded, pilled, prilled, or formed using conventional techniques into any desired shape, preferably one with a high surface area to volume ratio which is mechanically strong and allows free flow of liquids.

To improve material handling it may be beneficial to add conventional solid supports to or around the solid caustic. Thus the caustic solids can be mixed with activated carbon, porous resins, woods, fibers and the like. When a support is used it preferably comprises a minority of the reactive solid, so that a majority, by weight, of the reactive solid used in the bed is caustic.

Alternatively the solid caustic may be in baskets or fiber bags, perforated tubes, trays or the like. This will reduce the effectiveness of the process, but minimize material handling concerns.

QUADRIPHASE EXTRACTION CONDITIONS

Like most inorganic reactions, the reaction of halogen species, usually chlorides, with alkaline materials proceeds rapidly. The slow step or steps are likely to be in transport of acidic components through the hydrocarbon phase to the aqueous phase.

In functional terms, contact should be long enough to remove at least a majority, and preferably more than 90%, and most preferably more than 95% of the acidic halides in the combined vapor and liquid streams in the reactor effluent.

The separators can operate at the same conditions as before. Most refinery separators will operate at between 50° and 180° F., and at a pressure intermediate that of the last reactor effluent and the discharge compressor pressure.

Entrainment of caustic or brine in gas is undesirable and the bed geometry should be configured as needed to ensure that an aqueous phase forms which can remain as a tightly held film on the solid caustic until a sufficient amount accumulates that drops form which can fall down. A conventional demister at the top of the bed, or above the bed but preferably within the separator, can be installed to reduce or eliminate entrainement.

In terms of space velocity, the GHSV may range from 100 to 100,000 and preferably from 1000 to 10,000 GHSV. In terms of what is found in most refineries, these existing vapor/liquid separators will be large enough to hold beds of the size needed to remove the desired amount of chlorides from reactor effluent.

Caustic is used stoichiometrically, not catalytically. Caustic is continuously consumed in my process and the solid bed will eventually need to be replenished. Although the process does not use a "catalyst" per se, and consumes itself for treating, the process operates a long time because the caustic is present in massive amounts as a solid rather than a dilute liquid or a diluted form of solid adsorbent, such as alumina impregnated with caustic.

My solid caustic bed will continue to reactively remove chlorides until caustic exhaustion causes a breakthrough $C_1$. At this point the process may be shut down briefly so that additional solid caustic can be added. Alternatives for continuous operation include a swing reactor system or continuous addition systems, such as a lock hopper above the solid caustic bed. These can be used to add solid caustic without stopping the flow of gas.

When a simple fixed bed treater in a V/L separator is used, the solid caustic may simply be dumped onto dumped structured packing. Large pellets of caustic, with great mechanical strength, will minimize pressure drop across the bed and minimize caustic breakage. The separator preferably contains structured packing (~0–5% of separator volume) in a lower portion and solid caustic (70–90% of volume). About 10–30% at the top can be empty. Either upflow, downflow or cross-flow operation is possible.

A preferred configuration is split flow, with a two phase mixture charged to the middle portion of a bed, or intermediate two beds, one above and one below the inlet. The upper bed will treat the gas phase, and even may act to some extent as a demister, while the lower bed will treat the liquid phase.

EXPERIMENTS

I conducted experiments to simulate the process for removing chlorides from a two phase mixture by passing bone dry nitrogen gas through a bed of pellets of NaOH which had been soaked in liquid reformate. This simulated the treating of reformer effluent containing both vapor and liquid. The data showed that the operation could be continued a long time, with the net chloride content of the gas being removed as brine.

Although not a test of reformer effluent separation and neutralization, the tests did show that a reformate filled bed of solid caustic could remove chlorides from vapor streams. By controlling water addition to the unit, to maintain just enough water so that a nearly neutral brine can form and drain, it is possible to operate the process effectively for chloride removal and to extent the run for a long time without plugging the bed.

Although the quadriphase extraction process works, it may add more moisture to the recycle gas than would be the case if a completely dry process were used, such as alumina treaters or the dry caustic treating process.

DISCUSSION

The process of the present invention gives refiners a way to efficiently address their chloride problems. No longer will plant operators have to treat many streams coming from a single unit—they need only treat the reactor effluent vapor.

For refiners choosing to continue to use alumina treaters for reformate recycle or off gas, the process of the present invention provides a way to greatly lengthen the cycle length between bed polymer removal treatments.

By using existing equipment, such as one or more vapor/liquid separators associated with modern reformers, it is possible to have the benefits of recycle gas treating, or reformate treating, or preferably both, without the capital costs associated with a separate treating vessel.

I claim:

1. A process for removing acidic halides in a vapor and hydrocarbon liquid two-phase mixture and separating said mixture into a vapor phase and a liquid phase comprising:
   a. charging to a vapor/liquid separator operating at vapor/liquid separation conditions a two phase mixture of liquid hydrocarbons and vapor, and wherein said liquid, said vapor or both contain acidic halogen components;
   b. separating said two phase mixture into a vapor rich phase and a liquid phase in said separator and removing within said separator at least a majority of said acidic halogen components by reaction with a solid alkaline reagent within said separator;
   c. separately removing a vapor phase and a liquid phase from said separator as a product of the process.

2. The process of claim 1 wherein said alkaline reagent is alumina promoted with caustic.

3. The process of claim 1 wherein said alkaline reagent is charcoal impregnated with caustic.

4. The process of claim 1 wherein said alkaline reagent is solid caustic.

5. The process of claim 4 wherein said solid caustic comprises NaOH, KOH or mixtures thereof.

6. The process of claim 4 wherein said solid caustic is NaOH.

7. The process of claim 4 wherein said solid caustic is contained in porous bags, perforated pipe, or screens.

8. The process of claim 1 wherein said acidic halides are chlorides.

9. The process of claim 1 wherein chlorides are removed from a reforming reactor effluent consisting of a hydrogen rich gas phase and liquid reformate.

10. The process of claim 1 wherein a bed of low surface area, non-porous solid caustic particles is provided within said separator, and a water content in said two phase mixture is controlled to provide enough water to form a brine phase on said solid caustic particles.

11. The process of claim 10 wherein a brine stream is at least intermittently withdrawn from said separator, and water addition to said two phase mixture is controlled to maintain a brine pH of from 7 to 9.

12. The process of claim 1 wherein said two phase mixture is charged to an intermediate location of a neutralizing bed within said separator, and said vapor phase passes up through an upper portion of said neutralizing bed and said liquid phase passes down through said neutralizing bed.

13. The process of claim 1 where two neutralizing beds are located within said separator, said two-phase mixture is added to said separator intermediate said beds, and said vapor phase passes up through an upper neutralizing bed and said liquid phase passes down through a lower neutralizing bed.

14. A reforming process comprising:
   a. charging to a reforming reactor containing a chlorine and platinum containing reforming catalyst operating at reforming conditions a naphtha boiling range feed and a recycle hydrogen gas stream to produce a reforming reactor effluent comprising hydrogen rich vapor and naphtha boiling range reformate and chlorides;
   b. cooling said reactor effluent to produce a two phase mixture;
   c. neutralizing and separating said two phase mixture in a neutralizing separator comprising:
      an inlet for a two phase, vapor liquid mixture,
      an outlet in an upper portion thereof for a vapor phase,
      an outlet in a lower portion thereof for a liquid phase, and
      a bed of solid alkaline neutralizing material disposed within said separator at an elevation intermediate said upper portion and said lower portion, and in a location within said separator wherein said neutralizing material is continuously or intermittently contacted by reformate liquid;
   d. removing from said separator a neutralized vapor stream and recycling at least a portion thereof to said reforming reactor, and
   e. removing from said separator a liquid reformate fraction as a product of the process.

15. The process of claim 14 wherein said reformer comprises a low pressure vapor/liquid separator and a higher pressure recontacting drum,
   cooled reactor effluent is first charged to said low pressure separator,
   vapor from said low pressure separator is compressed to a higher pressure,
   liquid from said pressure separator is pumped and recontacted with compressed vapor from said low pressure separator to form a higher pressure mixture;
   said high pressure mixture is separated in said recontacting drum to produce a high pressure vapor phase at least a portion of which is recycled to said reforming reactor and a high pressure liquid phase which is removed as a product of the process,
   and wherein said alkaline reagent is present in at least one of said low pressure separator and said recontacting drum.

16. The process of claim 14 wherein said alkaline reagent is present in both said low pressure separator and said recontacting drum.

17. The process of claim 14 wherein valves and bypass piping are provided so that at least one of said low pressure separator and said recontacting drum is removed from service and bypassed without interrupting recycle gas flow to said reforming reactor and alkaline reagent is replaced and/or regenerated in said vessel which was removed from service.

\* \* \* \* \*